United States Patent
Greene et al.

(10) Patent No.: US 10,144,880 B2
(45) Date of Patent: Dec. 4, 2018

(54) CONVERSION OF TRIACYLGLYCERIDES-CONTAINING OILS TO JET FUEL RANGE HYDROCARBONS

(71) Applicants: Chevron Lummus Global, LLC, Bloomfield, NJ (US); Applied Research Associates, Inc., Albuquerque, NM (US)

(72) Inventors: Marvin I. Greene, Clifton, NJ (US); Ujjal K. Mukherjee, Montclair, NJ (US); Arun Arora, Edison, NJ (US); Edward Coppola, Albuquerque, NM (US); Charles Red, Jr., Albuquerque, NM (US); J. Steven Baxley, Albuquerque, NM (US); Sanjay Nana, Albuquerque, NM (US); Jeffrey Rine, Albuquerque, NM (US)

(73) Assignees: Chevron Lummus Global, LLC, Bloomfield, NJ (US); Applied Research Associates, Inc., Albuquerque, NM (US)

( * ) Notice: Subject to any disclaimer, the term of this patent is extended or adjusted under 35 U.S.C. 154(b) by 0 days.

(21) Appl. No.: 14/651,611

(22) PCT Filed: Dec. 4, 2013

(86) PCT No.: PCT/US2013/073121
§ 371 (c)(1),
(2) Date: Jun. 11, 2015

(87) PCT Pub. No.: WO2014/093097
PCT Pub. Date: Jun. 19, 2014

(65) Prior Publication Data
US 2015/0329788 A1    Nov. 19, 2015

Related U.S. Application Data

(63) Continuation of application No. 13/711,111, filed on Dec. 11, 2012, now Pat. No. 9,162,938.

(51) Int. Cl.
*C07C 1/20* (2006.01)
*C10G 3/00* (2006.01)
(Continued)

(52) U.S. Cl.
CPC ............ *C10G 3/50* (2013.01); *B01J 19/0046* (2013.01); *C07C 1/22* (2013.01); *C10G 3/40* (2013.01);
(Continued)

(58) Field of Classification Search
CPC ................. C07C 1/22; C07C 2/20; C07C 2/50
(Continued)

(56) References Cited

U.S. PATENT DOCUMENTS 3,394,074 A   7/1968   Buchmann et al.
4,990,243 A   2/1991   Winslow et al.
(Continued)

FOREIGN PATENT DOCUMENTS

JP   2007-131595 A   5/2007
JP   2008-297452 A   12/2008
(Continued)

OTHER PUBLICATIONS

Non-Final Office Action dated Dec. 3, 2015 in related U.S. Appl. No. 14/869,275 (25 pages).
(Continued)

*Primary Examiner* — Youngsul Jeong
(74) *Attorney, Agent, or Firm* — Osha Liang LLP

(57) ABSTRACT

A process for converting triacylglycerides-containing oils into crude oil precursors and/or distillate hydrocarbon fuels is disclosed. The process may include: reacting a triacylglycerides-containing oil-water-diatomic hydrogen mixture at a temperature in the range from about 250° C. to about 560° C. and a pressure greater than about 75 bar to convert at least a portion of the triacylglycerides and recovering a
(Continued)

reaction effluent comprising water and one or more of isoolefins, isoparaffins, cycloolefins, cycloparaffins, and aromatics; and hydrotreating the reaction effluent to form a hydrotreated effluent.

33 Claims, 2 Drawing Sheets

(51) Int. Cl.
*C10G 45/02* (2006.01)
*C07C 1/22* (2006.01)
*B01J 19/00* (2006.01)
*C10G 45/32* (2006.01)
*C10G 45/06* (2006.01)
*C10G 45/08* (2006.01)
*C10G 45/10* (2006.01)
*C10G 45/00* (2006.01)
*C10G 47/16* (2006.01)
*C10G 65/12* (2006.01)

(52) U.S. Cl.
CPC .......... *C10G 3/42* (2013.01); *C10G 3/52* (2013.01); *C10G 45/00* (2013.01); *C10G 45/02* (2013.01); *C10G 45/06* (2013.01); *C10G 45/08* (2013.01); *C10G 45/10* (2013.01); *C10G 45/32* (2013.01); *C10G 47/16* (2013.01); *C10G 65/12* (2013.01); C10G 2300/1011 (2013.01); C10G 2300/1014 (2013.01); C10G 2300/1018 (2013.01); C10G 2300/202 (2013.01); C10G 2300/4081 (2013.01); C10G 2400/02 (2013.01); C10G 2400/04 (2013.01); C10G 2400/08 (2013.01); Y02P 30/20 (2015.11)

(58) Field of Classification Search
USPC .......................................... 585/254; 44/605
See application file for complete search history.

(56) References Cited

U.S. PATENT DOCUMENTS

| | | | |
|---|---|---|---|
| 5,069,890 A | 12/1991 | Dai et al. | |
| 5,071,805 A | 12/1991 | Winslow et al. | |
| 5,073,530 A | 12/1991 | Bezman et al. | |
| 5,141,909 A | 8/1992 | Bezman | |
| 5,277,793 A | 1/1994 | Bezman et al. | |
| 5,366,615 A | 11/1994 | Bezman | |
| 5,409,617 A | 4/1995 | Ross et al. | |
| 5,439,860 A | 8/1995 | Habib et al. | |
| 5,453,177 A | 9/1995 | Goebel et al. | |
| 5,593,570 A | 1/1997 | Habib et al. | |
| 5,817,901 A | 10/1998 | Trambouze et al. | |
| 5,959,167 A | 9/1999 | Shabtai et al. | |
| 5,986,022 A | 11/1999 | Austin et al. | |
| 6,180,845 B1 | 1/2001 | Catallo et al. | |
| 6,514,897 B1 | 2/2003 | Moy et al. | |
| 6,573,417 B1 | 6/2003 | Rice | |
| 6,693,225 B2 | 2/2004 | Boyer et al. | |
| 6,860,986 B2 | 3/2005 | Timken et al. | |
| 6,872,685 B2 | 3/2005 | Timken | |
| 6,902,664 B2 | 6/2005 | Timken | |
| 7,232,935 B2 | 6/2007 | Jakkula et al. | |
| 7,459,597 B2 | 12/2008 | Koivusalmi et al. | |
| 7,473,811 B2 | 1/2009 | Eilos et al. | |
| 7,501,546 B2 | 3/2009 | Koivusalmi et al. | |
| 7,511,181 B2 | 3/2009 | Petri et al. | |
| 7,556,728 B2 | 7/2009 | Lehtonen et al. | |
| 7,691,159 B2* | 4/2010 | Li .......................... C10L 1/026 44/306 | |
| 7,754,931 B2 | 7/2010 | Monnier et al. | |
| 7,846,323 B2 | 12/2010 | Abhari et al. | |
| 7,850,841 B2 | 12/2010 | Koivusalmi et al. | |
| 7,880,049 B2 | 2/2011 | Dumesic et al. | |
| 7,915,460 B2 | 3/2011 | Kalnes et al. | |
| 7,928,079 B2 | 4/2011 | Hrabie et al. | |
| 7,960,596 B2 | 6/2011 | Miller | |
| 7,964,761 B2 | 6/2011 | Zmierczak et al. | |
| 7,967,973 B2 | 6/2011 | Myllyoja et al. | |
| 7,982,075 B2 | 7/2011 | Marker et al. | |
| 7,982,076 B2 | 7/2011 | Marker et al. | |
| 7,982,077 B2 | 7/2011 | Kalnes et al. | |
| 7,982,078 B2 | 7/2011 | Brady et al. | |
| 7,982,079 B2 | 7/2011 | Marker et al. | |
| 7,989,671 B2 | 8/2011 | Strege et al. | |
| 7,998,339 B2 | 8/2011 | Myllyoja et al. | |
| 7,999,142 B2 | 8/2011 | Kalnes et al. | |
| 7,999,143 B2 | 8/2011 | Marker et al. | |
| 8,003,834 B2 | 8/2011 | Marker et al. | |
| 8,003,836 B2 | 8/2011 | Marker et al. | |
| 8,017,819 B2 | 9/2011 | Yao et al. | |
| 8,026,401 B2 | 9/2011 | Abhari et al. | |
| 8,039,682 B2 | 10/2011 | McCall et al. | |
| 8,053,615 B2 | 11/2011 | Cortright et al. | |
| 8,058,492 B2 | 11/2011 | Anumakonda et al. | |
| 8,066,867 B2 | 11/2011 | Dziabala et al. | |
| 8,067,653 B2 | 11/2011 | Bressler | |
| 8,067,657 B2 | 11/2011 | Duarte Santiago et al. | |
| 8,076,504 B2 | 12/2011 | Kubatova et al. | |
| 8,084,655 B2 | 12/2011 | Dindi et al. | |
| 8,142,527 B2 | 3/2012 | Herskowitz et al. | |
| 8,178,060 B2 | 5/2012 | Corradi et al. | |
| 8,217,210 B2 | 7/2012 | Agrawal et al. | |
| 8,221,706 B2 | 7/2012 | Petri et al. | |
| 8,231,804 B2 | 7/2012 | Abhari | |
| 8,231,847 B2 | 7/2012 | da Silva Ferreira Alves et al. | |
| 9,206,367 B2 | 12/2015 | Seames et al. | |
| 2004/0045870 A1 | 3/2004 | Wrisberg et al. | |
| 2007/0137097 A1* | 6/2007 | Ikura ........................ C11C 3/00 44/308 | |
| 2007/0170091 A1 | 7/2007 | Monnier et al. | |
| 2007/0175795 A1 | 8/2007 | Yao et al. | |
| 2008/0071125 A1 | 3/2008 | Li | |
| 2008/0163543 A1 | 7/2008 | Abhari et al. | |
| 2009/0031617 A1 | 2/2009 | O'Rear | |
| 2009/0062578 A1 | 3/2009 | Koivusalmi et al. | |
| 2009/0077864 A1 | 3/2009 | Marker et al. | |
| 2009/0182106 A1 | 7/2009 | Parola et al. | |
| 2009/0287029 A1* | 11/2009 | Anumakonda ........ C10G 45/72 585/16 | |
| 2009/0300970 A1 | 12/2009 | Perego et al. | |
| 2010/0000908 A1 | 1/2010 | Markkanen et al. | |
| 2010/0036183 A1 | 2/2010 | Gudde et al. | |
| 2010/0043278 A1 | 2/2010 | Brevoord et al. | |
| 2010/0113848 A1 | 5/2010 | Strege et al. | |
| 2010/0160698 A1 | 6/2010 | Perego et al. | |
| 2010/0163458 A1 | 7/2010 | Daudin et al. | |
| 2010/0237853 A1 | 9/2010 | Bose et al. | |
| 2010/0240942 A1 | 9/2010 | Daudin et al. | |
| 2010/0256428 A1 | 10/2010 | Marker et al. | |
| 2010/0317903 A1 | 12/2010 | Knuuttila | |
| 2011/0028773 A1 | 2/2011 | Subramaniam et al. | |
| 2011/0071327 A1 | 3/2011 | Abhari et al. | |
| 2011/0092746 A1 | 4/2011 | Dalloro et al. | |
| 2011/0105814 A1 | 5/2011 | Koivusalmi et al. | |
| 2011/0113679 A1* | 5/2011 | Cohen .................... C10G 45/00 44/388 | |
| 2011/0131867 A1 | 6/2011 | Kalnes et al. | |
| 2011/0155631 A1 | 6/2011 | Knuuttila et al. | |
| 2011/0160482 A1 | 6/2011 | Nagaki et al. | |
| 2011/0166396 A1 | 7/2011 | Egeberg et al. | |
| 2011/0209387 A1 | 9/2011 | Humphreys | |
| 2011/0230572 A1 | 9/2011 | Allison et al. | |
| 2011/0237838 A1 | 9/2011 | Zmierczak et al. | |
| 2011/0239532 A1 | 10/2011 | Baldiraghi et al. | |
| 2011/0289826 A1 | 12/2011 | Srinakruang | |
| 2011/0313219 A1 | 12/2011 | Fernando et al. | |
| 2011/0315596 A1 | 12/2011 | Prentice et al. | |
| 2012/0016167 A1 | 1/2012 | Hanks | |
| 2012/0094879 A1 | 4/2012 | Roberts et al. | |
| 2012/0095274 A1 | 4/2012 | Bao et al. | |

(56) References Cited

U.S. PATENT DOCUMENTS

| | | |
|---|---|---|
| 2012/0142984 A1 | 6/2012 | Roberts et al. |
| 2012/0157734 A1 | 6/2012 | Strege et al. |
| 2013/0247451 A1* | 9/2013 | Vanhercke ............ C07K 14/415 44/388 |

FOREIGN PATENT DOCUMENTS

| | | |
|---|---|---|
| WO | 2008020048 A2 | 2/2008 |
| WO | 2009015054 A1 | 1/2009 |
| WO | 2010011737 A2 | 1/2010 |
| WO | 2010053896 A2 | 5/2010 |

OTHER PUBLICATIONS

International Search Report and Written Opinion dated Mar. 27, 2014 in corresponding International Application No. PCT/US2013/073132 (14 pages).

Correspondence reporting an Official Letter and Search Report (w/translation) dated Jan. 19, 2015 in corresponding Taiwan application No. 102145419 (11 pages).

International Search Report issued in PCT/US2013/073121 dated Mar. 27, 2014 (2 pages).

Written Opinion of the International Searching Authority issued in in PCT/US2013/073121 dated Mar. 27, 2014 (7 pages).

Notice of Reasons for Rejection dated Mar. 15, 2016 in corresponding Japanese application No. 2015-537029 with English translation (7 pages).

Extended European Search Report dated Jul. 12, 2016 in corresponding European application No. 13862605.6 (8 pages).

Lin Chen et al: "Biodiesel production from algae oil high in free fatty acids by two-step catalytic conversion"; Bioresource Technology, Elsevier BV, GB, vol. 111, Feb. 7, 2012; pp. 208-214.

Frohlich A et al: "Evaluation of Camelina sativa oil as a feedstock for biodiesel production", Industrial Crops NAD Products, Elsevier, NL, vol. 21, No. 1, Jan. 1, 2005; pp. 25-31.

Office Action issued in related U.S. Appl. No. 14/885,135 dated Aug. 10, 2017 (75 pages).

* cited by examiner

CONVERSION OF TRIACYLGLYCERIDES-CONTAINING OILS TO JET FUEL RANGE HYDROCARBONS

FIELD OF THE DISCLOSURE

Embodiments disclosed herein relate generally to production of useful hydrocarbons, such as distillate fuels, from triacylglycerides-containing plant or animal fats-containing oils. More particularly, embodiments disclosed herein relate to production of jet fuel range hydrocarbons from triacylglycerides-containing plant or animal fats-containing oils.

BACKGROUND

Hydrothermolysis of triacylglycerides-containing oils such as those derived from crops, animal fats or waste vegetable and animal-derived oils involves many types of chemical reactions. As one example, some prior art processes catalytically hydrotreat C10 to C18 triacylglyceride containing oils, converting the unsaturated aliphatic chains in the triacylglyceride containing oils to straight chain paraffins while simultaneously deoxygenating/decarboxylating the acid and glyceryl groups to form water, carbon dioxide and propane. Two downstream processes are then required to (a) skeletally isomerize the n-paraffins to isoparaffins to produce specification grade diesel fuels, and (b) hydrocracking the diesel range n-paraffins and isoparaffins to hydrocarbons to produce specification grade jet fuels.

U.S. Pat. No. 7,691,159, for example, discloses a hydrothermolysis process to convert triacylglycerides to smaller organic acids in the presence of hot compressed water at supercritical water conditions. During the process, the backbone of the triacylglycerides undergoes rearrangement reactions.

SUMMARY OF THE DISCLOSURE

In one aspect, embodiments disclosed herein relate to a process for converting triacylglycerides-containing oils into crude oil precursors and/or distillate hydrocarbon fuels. The process may include: reacting a mixture comprising water, diatomic hydrogen, and a triacylglycerides-containing oil comprising at least 20 wt % C20 to C24 fatty acids at a temperature in the range from about 250° C. to about 560° C. and a pressure greater than about 75 bar to convert at least a portion of the triacylglycerides and recovering a reaction effluent comprising water and one or more of isoolefins, isoparaffins, cycloolefins, cycloparaffins, and aromatics; and hydrotreating the reaction effluent to form a hydrotreated effluent.

In another aspect, embodiments disclosed herein relate to a process for converting triacylglycerides-containing oils into crude oil precursors and/or distillate hydrocarbon fuels. The process may include: subjecting one or more triacylglycerides-containing oils to a conversion process to convert at least a portion of the triacylglycerides to produce a reaction product comprising one or more of isoolefins, isoparaffins, cycloolefins, cycloparaffins, and aromatics boiling in the range of naphtha, diesel, and jet fuels; varying a composition of the triacylglycerides-containing oils to selectively vary a yield of the jet range products. The varying may include, for example, increasing or decreasing a content of camelina-based oils, *carinata*-based oils, *lesquerella*-based oils, physaria-based oils, or mixtures thereof in the triacylglycerides-containing oil, thereby affecting the overall jet yield of the process.

Other aspects and advantages will be apparent from the following description and the appended claims.

DETAILED DESCRIPTION

Figure 1:
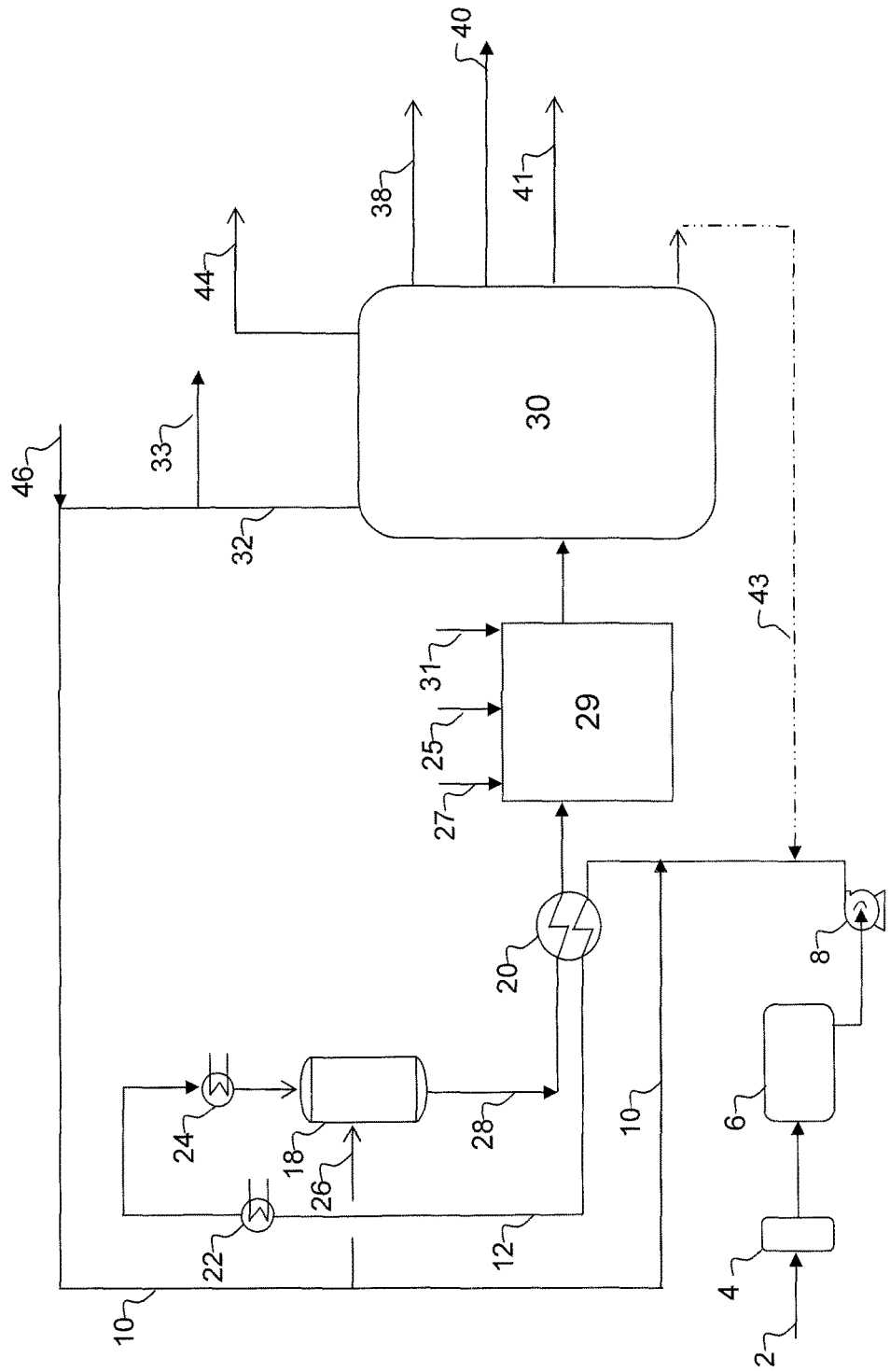
FIG. 1 is a simplified process flow diagram of a process according to embodiments herein.

In one aspect, embodiments disclosed herein relate generally to production of useful hydrocarbons, such as paraffins, from triacylglycerides-containing oils, such as from renewable feedstocks. In another aspect, embodiments disclosed herein relate to processes and systems for converting triacylglycerides-containing oils into crude oil precursors and/or distillate hydrocarbon fuels.

Renewable feedstocks having triacylglycerides-containing oils useful in embodiments disclosed herein may include fatty acids, saturated triacylglycerides, and triacylglycerides having one or more olefinic bonds. For example, triacylglycerides-containing oils may include oils from at least one of camelina, *carinata, lesquerella*, physaria, jatropha, karanja, moringa, palm, castor, cotton, corn, linseed, peanut, soybean, sunflower, tung, babassu, and canola, or at least one triacylglycerides-containing oil from at least one of, shea butter, tall oil, tallow, waste vegetable oil, algal oil, and pongamia.

A mixture of the triacylglycerides-containing oil with water and hydrogen, fed as $H_2$, diatomic hydrogen, may be reacted at a temperature in the range from about 250° C. to about 560° C. and a pressure greater than about 75 bar to convert at least a portion of the triacylglycerides to a hydrocarbon or mixture of hydrocarbons comprising one or more of isoolefins, isoparaffins, cycloolefins, cycloparaffins, and aromatics. In some embodiments, the reaction conditions are such that the temperature and pressure are above the supercritical temperature and pressure of water. The resulting reaction effluent may then be further treated and separated to recover the hydrocarbon products.

To form the triacylglycerides-water-hydrogen mixture, a triacylglycerides-containing oil may be mixed with water and diatomic hydrogen in any order or with a mixture of water and diatomic hydrogen.

At supercritical water hydrothermolysis reaction conditions, protonic hydrogen may be generated in situ. For example, U.S. Pat. No. 7,691,159 hypothesizes that, for each mole of soybean oil, 1.5 moles of $H_2$ are extracted from the water and added to the resulting hydrocarbon. While presenting this in terms of diatomic hydrogen equivalents, the in situ derived protonic hydrogen atoms would rapidly react and incorporate into the carboxylate molecules derived from the triacylglycerides. The diatomic hydrogen feed used in embodiments herein is in addition to any monoatomic hydrogen that may be generated in situ from water or other components in the hydrothermolysis reactor, and, although being an additional operating expense, may provide the benefits of enhanced reactivity within the hydrothermolysis reactor as well as an increased H/C ratio in the resulting product. Externally supplied diatomic hydrogen also provides an independent means of controlling the process performance, which cannot be obtained via in situ monoatomic hydrogen production alone, as it is dependent upon the hydrothermolysis reaction conditions and the composition of the triacylglycerides-containing feedstock. Overall, adding an external supply of diatomic hydrogen to the catalytic hydrothermolysis reactor, along with the super critical water and the renewable oil feed provides a different process, different reaction mechanism, and added performance over in situ monoatomic hydrogen generation alone.

Another advantage of co-feeding externally supplied diatomic hydrogen to the catalytic hydrothermolysis reactor is the hydrogen capping effect of stabilizing any free radicals formed during the catalytic hydrothermolysis reactions, thereby avoiding formation of oligomeric and/or polymeric materials, often referred to as coke or coke precursors or coke deposits, that would otherwise form as a result of condensation of these free radicals. Thus, co-feeding externally supplied diatomic hydrogen provides improved on-stream operability relative to processes that do not co-feed diatomic hydrogen gas.

In some embodiments, to form the triacylglycerides-water-diatomic hydrogen mixture, triacylglycerides-containing oil is first mixed with water to form a triacylglyceride-water mixture. The resulting triacylglycerides-water mixture is then mixed with diatomic hydrogen to form the triacylglycerides-water-diatomic hydrogen mixture.

The triacylglycerides-water-diatomic hydrogen mixture may have a water to triacylglycerides mass ratio in the range from about 0.001:1 to about 1:1 in some embodiments; from about 0.01:1 to about 1:1 in other embodiments; and from about 0.1:1 to about 1:1 in yet other embodiments.

The triacylglycerides-water-diatomic hydrogen mixture may have a diatomic hydrogen to triacylglycerides mass ratio in the range from about 0.001:1 to about 1:1 in some embodiments; from about 0.005:1 to about 0.5:1 or 1:1 in other embodiments; from about 0.01:1 to about 0.5:1 in other embodiments; and from about 0.1:1 to about 0.5:1 in yet other embodiments. In some embodiments, the diatomic hydrogen to triacylglycerides mass ratio may be in the range from about 0.1:1 to about 0.2:1. The total diatomic hydrogen feed rate in some embodiments may be sufficient to supply a portion or all of the hydrogen necessary for the hydrothermolysis as well as any close-coupled downstream processing steps, such as hydrotreatment.

The reaction effluent may then be directly catalytically hydrotreated, without intermediate separations of water, unreacted diatomic hydrogen, or other light gas byproducts, to form additional distillate range hydrocarbons and/or to convert precursors in the reaction effluent to distillate range hydrocarbons. Homogeneously catalyzed hydrothermolysis produces a crude oil that requires heterogeneously catalyzed hydrotreatment to be converted to useful infrastructure-compatible distillate fuels. Catalytic hydrotreatment processes may operate at elevated pressures, such as 500-2000+ psig, using supported catalysts having activity towards both heteroatom removal and double bond saturation reactions. Also required is an excess flow of diatomic hydrogen gas over and above the stoichiometric requirement, which for the case of catalytic hydrothermolysis-derived crude oil feedstocks may be in the range of 1000 to 2000 scf per barrel, the latter depending upon renewable feedstock type and catalytic hydrothermolysis reaction conditions. The need for excess diatomic hydrogen gas is to: a) drive the desired hydrotreatment reactions to a high degree of conversion; and b) to provide a heat sink to control unmanageable exotherms that would otherwise result from the high heats of hydrotreatment reactions. The adiabatic temperature rise, i.e., the temperature increase from reactant inlet stream to product effluent stream across the hydrotreating catalyst bed, can amount to about 180-200° F. per each thousand standard cubic feet hydrogen consumed. An advantage of co-feeding externally supplied diatomic hydrogen to the hydrothermolysis reactor is that the diatomic hydrogen contained in the effluent gas stream from the catalytic hydrothermolysis reactor can provide a part or all of the diatomic hydrogen gas feed requirement for the downstream catalytic hydrotreating reactor, as well as enhancing the reaction within the catalytic hydrothermolysis reactor itself, as discussed above.

In some embodiments, the above-mentioned triacylglycerides-containing oils, following hydrothermolysis, may be co-processed in the hydrotreatment zone with other hydrocarbon feedstocks, such as atmospheric gas oil (AGO), vacuum gas oil (VGO), or other feeds derived from petroleum, shale oil, tar sands, coal-derived oils, organic waste oils, and the like.

Following hydrotreatment, the hydrotreatment effluent may then be processed to separate water, unreacted diatomic hydrogen, and light gases from the hydrotreatment effluent and to fractionate the hydrocarbons into one or more hydrocarbon fractions, such as those boiling in the range of naphtha, diesel, or jet. The water and diatomic hydrogen may then be recycled for admixture with the triacylglycerides-containing oil as described above.

The reaction of the triacylglycerides to produce hydrocarbons may be primarily one or more hydrothermolysis reactions catalyzed by water and performed at a reaction temperature in the range from about 250° C. to about 560° C.; from about 375° C. to about 550° C. in some embodiments; and from about 425° C. to about 525° C. in other embodiments. Reaction conditions may also include a pressure of greater than 75 bar; greater than 150 bar in other embodiments; greater than 200 bar in other embodiments; between about 75 bar and about 300 bar in some embodiments; and between about 150 bar and about 250 bar in other embodiments. Conditions of temperature and/or pressure may be selected to be above the critical temperature and/or pressure of water. In all embodiments, the hydrothermolysis reactions may be performed in the absence of added catalysts, such as an inorganic heterogeneous catalyst or a soluble metallic catalyst.

Referring now to FIG. 1, a simplified process flow diagram of a process for converting triacylglycerides-containing oils into crude oil precursors and/or distillate hydrocarbon fuels according to embodiments herein is illustrated. A triacylglycerides-containing oil may be provided to the system via flow line 2, filtered if necessary in a filter 4, and stored in feed tank 6. The triacylglycerides-containing oil may then be fed via pump 8 and mixed with water fed via flow line 10. Mixing of the triacylglycerides-containing oil with water may be performed in a mixing device, such as a mixing tee, an agitated vessel, an in-line mixer or other mixing devices as known to those of skill in the art.

The triacylglycerides-water mixture 12 may then be combined with diatomic hydrogen fed via flow line 14 to form a triacylglycerides-water-diatomic hydrogen mixture 16. Mixture 16 may then be fed to hydrothermolysis reactor 18 and maintained at reaction conditions for a time sufficient to convert at least a portion of the triacylglycerides to distillate hydrocarbons or precursors thereof. Reaction conditions may include a temperature in the range from about 250° C. to about 560° C. and a pressure of at least 75 bar. The residence time required in reactor 18 to convert the triacylglycerides may vary depending upon the reaction conditions as well as the specific triacylglycerides-containing oil used. In some embodiments, residence times in reactor 18 may be in the range from about 3 to about 6 minutes. To elevate the temperature of the feed to reaction conditions, heat may be supplied to the feed via one or more of a feed-effluent exchanger 20, an indirect heat exchanger 22 to heat the triacylglycerides-water mixture 12, and an indirect heat exchanger 24 to heat the triacylglycerides-water-diatomic hydrogen mixture 16, among other options. The hydrothermolysis reaction can also include some exothermic reactions, which may supply additional heat to maintain the required reaction temperature conditions and to reduce external heat input requirements. In some embodiments, one or more water feed lines 26 may be provided to control the exotherm and the temperature or temperature profile in hydrothermolysis reactor 18.

Following reaction of the triacylglycerides in hydrothermolysis reactor 18, the reaction effluent 28 may be used to preheat the feed in feed-effluent exchanger 20, and further processed to recover the distillate hydrocarbons. For example, hydrothermolysis effluent 28 may then be fed, without separation of the water from the hydrothermolysis effluent, to a hydrotreatment system 29 to further treat the effluent. Hydrotreatment system 29 may include one or more reactors (hydrotreaters) (not shown) containing a hydroconversion catalyst to convert at least a portion of the hydrothermolysis effluent to distillate hydrocarbons. Additional diatomic hydrogen, if necessary, may be added to hydrotreatment system 29 via flow line 27. Further, as noted above, additional hydrocarbon feedstocks may be co-processed with hydrothermolysis effluent 28, and may be fed to hydrotreatment system 29 via flow line 25. Non-renewable hydrocarbon feedstocks, for example, may include one or more of petroleum distillates; shale oil distillates; tar sands-derived distillates; coal gasification byproduct oils; and coal pyrolysis oils, among others. If necessary, some sulfur-containing compound such as, for example, dimethyl disulfide dissolved in a suitable hydrocarbon solvent, may be fed to hydrotreatment system 29 via flow line 31 in order to maintain the catalysts in their most active states.

The hydrothermolysis reactor and the hydrotreatment system may be "close-coupled," where the effluent from the hydrothermolysis reaction step is passed to the hydrotreatment system 29 without phase separation (no separation of water, oil, and diatomic hydrogen). In some embodiments, the effluent from the hydrothermolysis reaction step may be passed to the hydrotreatment system under autogeneous pressure, i.e., without any pressure letdown between hydrothermolysis and hydrotreatment other than that which may occur by normal flow-induced pressure drops in piping and feed-effluent heat exchangers. In some embodiments, the effluent from the hydrothermolysis reaction step may be passed to the hydrotreatement system with pressure let down to a lower pressure level of the hydrotreatment system. Additionally, due to the diatomic hydrogen feed to the hydrothermolysis reactor, little or no additional diatomic hydrogen, and thus minimal or no hydrogen compression or re-compression is necessary for hydrotreatment. Due to compatible reaction conditions, including pressures and diatomic hydrogen to triacylglycerides ratios, and space velocities, the diatomic hydrogen may be carried through the entire reaction system, providing enhanced system performance including suppressed coking rates and at higher thermal efficiencies and lower cost.

The hydrotreatment effluent 34 may then be fed to effluent treatment system 30 for separation and recovery of reaction products. Effluent treatment system 30 may, for example, separate water 32 and diatomic hydrogen 36 from the hydrocarbons. The resulting hydrocarbons may also be fractionated into two or more fractions, which, as illustrated, may include distillate hydrocarbons boiling in the range of naphtha 38, diesel 41, or jet 40, and vacuum gas oil (VGO) 42. Some offgas 44 may also be produced.

As noted above, the effluent from the hydrothermolysis reaction step may be close-coupled, being passed to the hydrotreatment system 29 under autogeneous pressure, i.e., without any pressure letdown between hydrothermolysis and hydrotreatment other than that which may occur by normal flow-induced pressure drops in piping and feed-effluent heat exchangers. In such embodiments, a pressure letdown valve or valves 35 may be provided intermediate hydrotreatment system 29 and separation system 30 to decrease the pressure from an autogeneous pressure, for example, at or above the supercritical pressure of water, to a pressure less than the supercritical pressure of water, such as atmospheric pressure, in one or more letdown steps. The pressure letdown system may also provide for an initial phase separation of light gases (including diatomic hydrogen), water, and hydrocarbons.

A portion of water fraction 32 may be purged via flow line 33, if and as necessary, to avoid buildup of organic acids or other reaction byproducts. The water fraction 32 and the diatomic hydrogen fraction 36 may then be recycled and combined, as necessary, with makeup water 46 and makeup diatomic hydrogen 48, respectively, for mixture with the triacylglycerides-containing oil as described above. Compressor 52 may be used to pressurize the diatomic hydrogen recycle. In some embodiments, a heavy hydrocarbon recycle fraction 43 may also be recovered, and may be recycled to the hydrothermolysis reactor system 18, hydrotreatment system 29, or a combination thereof.

Figure 2:
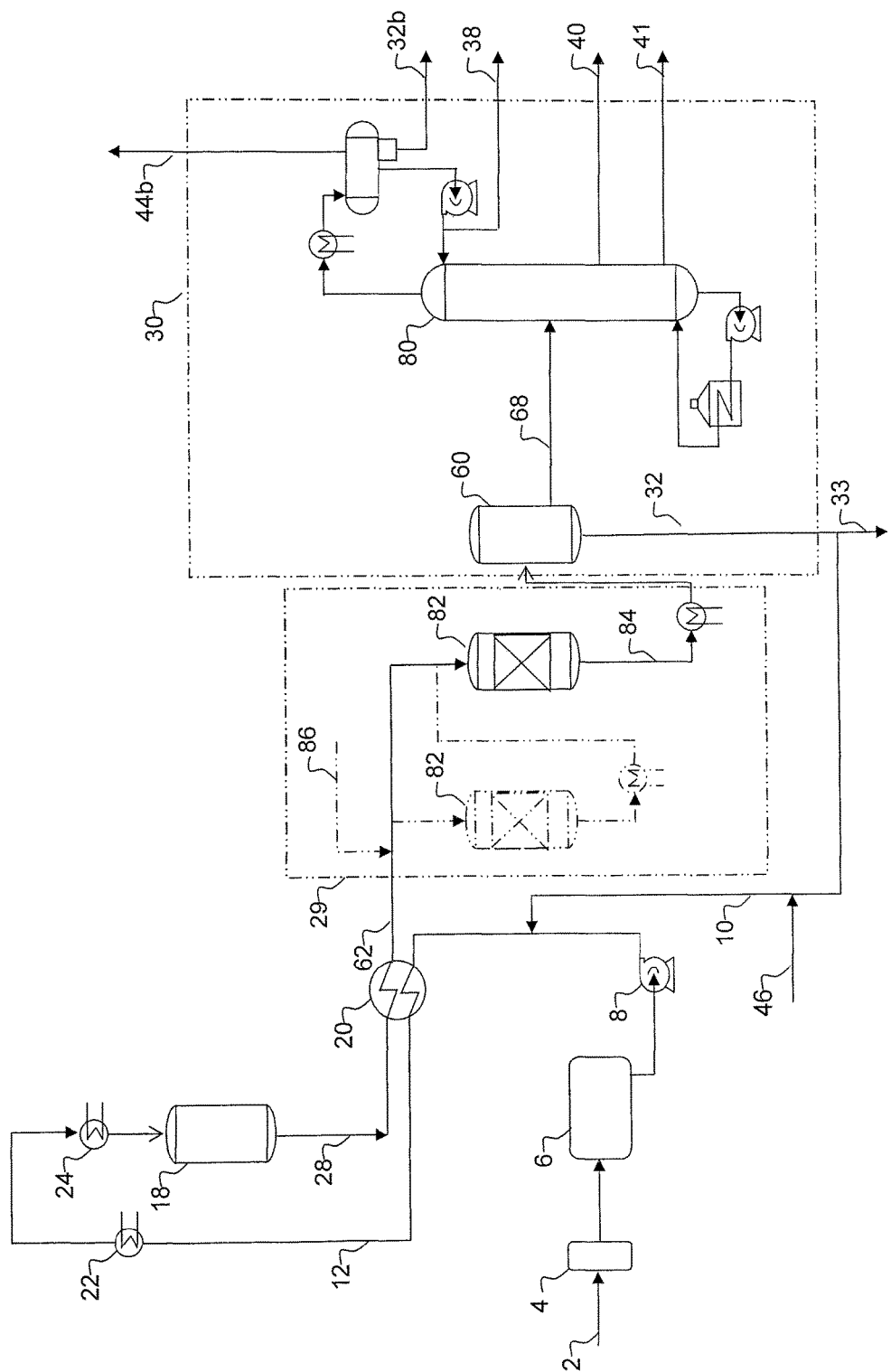
FIG. 2 is a simplified process flow diagram of a process according to embodiments herein.

Referring now to FIG. 2, a simplified process flow diagram of a process for converting triacylglycerides-containing oils into crude oil precursors and/or distillate hydrocarbon fuels according to embodiments herein is illustrated, where like numerals represent like parts. In this embodiment hydrotreatment system 29 may include a hydrotreater 82 for further converting the crude oil precursors and/or distillate hydrocarbon fuels in hydrothermolysis effluent 28. The hydrothermolysis effluent 28, 62, including diatomic hydrogen and water, may be fed to a hydrotreater 82 and contacted with a suitable catalyst to produce desired end products, such as jet, naphtha, and diesel boiling range hydrocarbons. If necessary, additional diatomic hydrogen may be added to the hydrothermolysis effluent prior to hydrotreatment via flow line 86.

Following hydrotreatment, the hydrotreated effluent 84 may then be fed to effluent treatment system 30. As illustrated in FIG. 2, effluent treatment system 30 may include a drum 60 for separation of the gaseous components from the liquid components in the cooled effluent 62. The gaseous components, including diatomic hydrogen and possibly some light reaction byproducts, may be recovered from drum 60 via flow line 64. Liquid components may settle in the bottom of drum 60, resulting in formation of a two-phase system, where the water may be recovered via flow line 32 and the hydrocarbons may be recovered via flow line 68. The water fraction 32 recovered from drum 60 may then be purged and/or recycled as described above.

Following separations in drum 60, the gaseous products in flow line 64 may be separated via a gas separation device 70 to result in a recycle diatomic hydrogen fraction 36 and an off-gas fraction 44a, as described above. The liquid hydrocarbon products may then be fed to a fractionator 80 for separation of the hydrocarbons into one or more boiling range fractions including naphtha 38, jet 40, diesel 41, and vacuum gas oil (VGO) 42. An additional off-gas fraction 44b and water fraction 32b may also result from separations in fractionator 80.

To produce additional distillate range fuels, such as where C20+ hydrocarbons are produced in hydrothermolysis reactor 18, some of the VGO fraction 42 may be recycled back to the hydrothermolysis reactor 18 for additional processing, such as via flow line 43.

As described with respect to the embodiments of FIGS. 1 and 2, there is no phase separation of the hydrothermolysis effluent before hydrotreatment. The hydrothermolysis step and feed of the entire hydrothermolysis effluent stream is performed in a close-coupled system, where no intermediate separations are performed. One skilled in the art may anticipate that such a close-coupled system would not be technically feasible, expecting the active metals in the supported catalysts to be solubilized or decrepitated. However, it has been found that catalyst activity may be maintained, over several hundred hours of pilot plant operations, even in the presence of high water concentrations and high organic acid concentrations (i.e., a much higher level of oxygenates than are normally encountered with typical petroleum feedstocks). Injection of water, hydrocarbons, free fatty acids, alcohols, and unconverted triacylglycerides directly to a hydrotreatment zone may thus provide for a significant reduction in unit operations and processing steps required to produce the desired distillate fuels.

Catalysts useful in hydrotreater 82 may include catalysts that may be used for the hydrotreating or hydrocracking of a hydrocarbon feedstock. In some embodiments, the hydrotreating catalyst may effectively hydrodeoxygenate and/or decarboxylate the oxygen bonds contained in the hydrotreater feed reduce or eliminate the organic acid concentration in effluent 28. In some embodiments, greater than 99%, 99.9%, or 99.99% of the organic acids may be converted over the hydrotreatment catalyst.

Hydrotreating catalysts that may be useful include catalysts selected from those elements known to provide catalytic hydrogenation activity. At least one metal component selected from Group 8-10 elements and/or from Group 6 elements is generally chosen. Group 6 elements may include chromium, molybdenum and tungsten. Group 8-10 elements may include iron, cobalt, nickel, ruthenium, rhodium, palladium, osmium, iridium and platinum. The amount(s) of hydrogenation component(s) in the catalyst suitably range from about 0.5% to about 10% by weight of Group 8-10 metal component(s) and from about 5% to about 25% by weight of Group 6 metal component(s), calculated as metal oxide(s) per 100 parts by weight of total catalyst, where the percentages by weight are based on the weight of the catalyst before sulfiding. The hydrogenation components in the catalyst may be in the oxidic and/or the sulfidic form. If a combination of at least a Group 6 and a Group 8 metal component is present as (mixed) oxides, it will be subjected to a sulfiding treatment prior to proper use in hydrocracking. In some embodiments, the catalyst comprises one or more components of nickel and/or cobalt and one or more components of molybdenum and/or tungsten or one or more components of platinum and/or palladium. Catalysts containing nickel and molybdenum, nickel and tungsten, platinum and/or palladium are useful.

In some embodiments, hydrotreater 82 may include two or more beds or layers of catalyst, such as a first layer including a hydrocracking catalyst and a second layer including a hydrotreating catalyst.

In some embodiments, the layered catalyst system may include a lower catalyst layer that includes a bed of a hydrocracking catalyst suitable for hydrocracking any vacuum gas oil (VGO) range hydrothermolysis products or added feeds to diesel range or lighter hydrocarbons. The hydrocracking catalysts used may also be selected to minimize or reduce dearomatization of the alkylaromatics formed in the hydrothermolysis reactor. VGO hydrocracking catalysts that may be used according to embodiments herein include one or more noble metals supported on low acidity zeolites wherein the zeolite acidity is widely distributed throughout each catalyst particle. For example, one or more catalysts as described in U.S. Pat. No. 4,990,243, U.S. Pat. No. 5,069,890, U.S. Pat. No. 5,071,805, U.S. Pat. No. 5,073,530, U.S. Pat. No. 5,141,909, U.S. Pat. No. 5,277,793, U.S. Pat. No. 5,366,615, U.S. Pat. No. 5,439,860, U.S. Pat. No. 5,593,570, U.S. Pat. No. 6,860,986, U.S. Pat. No. 6,902,664, and U.S. Pat. No. 6,872,685 may be used in embodiments herein, each of which are incorporated herein by reference with respect to the hydrocracking catalysts described therein. In some embodiments, the inclusion of the VGO hydrocracking may result in extinctive hydrocracking of the heavy hydrocarbons, such that the only net hydrocarbon products include diesel range and lighter hydrocarbons.

One skilled in the art will recognize that the various catalyst layers may not be made up of only a single catalyst, but may be composed of an intermixture of different catalysts to achieve the optimal level of metals and deoxygenation for that layer. Although some olefinic bond hydrogenation will occur in the lower portion of the zone, the removal of oxygen, nitrogen, and sulfur may take place primarily in the upper layer or layers. Obviously additional metals removal also will take place. The specific catalyst or catalyst mixture selected for each layer, the number of layers in the zone, the proportional volume in the bed of each layer, and the specific hydroprocessing conditions selected will depend on the feedstock being processed by the unit, the desired product to be recovered, as well as commercial considerations such as cost of the catalyst. All of these parameters are within the skill of a person engaged in the petroleum processing industry and should not need further elaboration here.

While the above-described systems are described with respect to a single hydrothermolysis reactor 18 and a single hydrotreater 82, the reaction zones may include two or more reactors arranged in series or in parallel. Likewise, back-up compressors, filters, pumps, and the like may also be used. Further, compressors may be single stage or multi-stage compressors, which in some embodiments may be used to compress a single gas stream in sequential stages or may be used to compress separate gas streams, depending on plant layout.

As described above with respect to FIG. 2, fractionator 80 may be used to recover various hydrocarbon fractions. Where hydrotreater 82 includes a bed or layer of hydrocracking catalyst, production of heavy hydrocarbons may be reduced or eliminated. In such embodiments where the heavy hydrocarbons are eliminated, fractionator 80 may be used to recover a diesel fraction as the bottoms from the column, and recycle of heavy hydrocarbons, such as VGO, may be unnecessary. When produced, the VGO may be recycled, as described above, or may be recovered as a low sulfur fuel oil product.

As described above, processes disclosed herein may be performed in a system or apparatus for converting triacylglycerides-containing oils into crude oil precursors and/or distillate hydrocarbon fuels. The system may include one or more mixing devices for mixing a triacylglycerides-containing oil feed with water and diatomic hydrogen. For example, the system may include a first mixing device for mixing a triacylglycerides-containing oil feed with water to form an oil-water mixture, and a second mixing device for mixing the oil-water mixture with diatomic hydrogen to form a feed mixture.

The resulting mixture may then be fed via a flow conduit to a hydrothermolysis reactor for reacting the feed mixture at a temperature in the range of 250° C. to about 560° C. and a pressure greater than about 75 bar to produce a reaction effluent. The hydrothermolysis reactor may include, for example, one or more tubular conduits within a furnace configured to maintain a temperature of the hydrothermolysis reactor effluent proximate an outlet of the hydrothermolysis reactor at reaction conditions, such as a temperature in the range from about 400° C. to about 560° C., or at a temperature and pressure greater than the critical temperature and pressure of water. The furnace may be, for example, an electrically heated furnace, or a furnace fired with a fuel gas, such as a natural gas, synthesis gas, or light hydrocarbon gases, including those produced in and recovered from the hydrothermolysis reactor. Reaction conditions may be achieved by use of one or more pumps, compressors, and heat exchangers. In other embodiments, the hydrothermolysis reactor may be an adiabatic reactor. A separator may then be used for separating water and hydrogen from hydrocarbons in the reaction effluent.

The system may also include a compressor for compressing diatomic hydrogen recovered from the separator, as well as one or more fluid conduits for recycling the compressed diatomic hydrogen and/or the recovered water to the mixing device for mixing diatomic hydrogen or the mixing device for mixing water. The system also includes a hydrotreater to hydrotreat at least a portion of the hydrothermolysis reaction effluent.

The system may also include a fractionator for fractionating hydrocarbons in the hydrotreater effluent to form one or more hydrocarbon fractions boiling in the naphtha, jet or diesel range.

To control reaction temperatures and exotherms in the hydrothermolysis reactor, the system may include one or more fluid conduits for injecting water into the hydrothermolysis reactor.

As described above, embodiments disclosed herein provide processes for the conversion of renewable feedstocks to infrastructure-compatible distillate fuels. For example, in some embodiments, the jet fraction recovered may have a total acid number of less than 0.1 in some embodiments, expressed as mg KOH per gram; less than 0.015 expressed as mg KOH per gram in other embodiments; and less than 0.010 in other embodiments. The jet may have an olefins content of less than about 5 vol % and an aromatics content of less than about 25 vol % in some embodiments. These properties, among others, may allow the jet and/or the diesel fractions produced in embodiments herein to be used directly as a fuel without blending. In some embodiments, the whole hydrocarbon liquid product recovered from the hydrotreatment reaction zone may be used to produce distillate fuels meeting military, ASTM, EN, ISO, or equivalent fuel specifications.

The process may be carried out in an economically feasible method at a commercial scale. Embodiments herein may maximize the thermal efficiency of the triacylglycerides-containing oil conversion in an economically attractive manner without being hampered by operability problems associated with catalyst fouling. During the hydrothermolysis process, water, such as about 5% of the feed water, may be consumed in the hydrolysis reaction. In the hydrotreater, much of the glycerin byproduct produced may be further hydrogenated and converted to propane. Diatomic hydrogen is consumed during the hydrotreating step, and the average specific gravity of the product may be reduced, such as from approximately 0.91 to about 0.81. Decarboxylation reactions form COx and that carbon loss may result in a reduced mass yield of liquid products, and an equivalent lower volumetric yield. The actual crude yield may be in the range from about 75% to about 90%, such as in the range from about 80% to 84%, depending on how the hydrothermolysis process is executed.

Naphtha, jet, and diesel fuels may be produced by processes disclosed herein. A higher boiling gas oil material may also be produced, and may contain high-quality, high hydrogen content paraffins in the C17 to C24 boiling range. These heavier hydrocarbons may be recycled to the hydrothermolysis reactor for further treatment and production of naphtha, jet, and diesel range products. Fuel gases (off gases) may also be produced, which may be used in some embodiments for process heat, hydrogen production, or recovered as individual products (LPG, ethylene, propylene, n-butane, iso-butane, etc.).

Fuels produced by embodiments herein may: contain cycloparaffins and aromatics; exhibit high density; exhibit high energy density; exhibit good low-temperature properties (freezing point, cloud point, pour point, and viscosity); exhibit natural lubricity; exhibit a wide range of hydrocarbon types and molecular weights similar to petroleum; and/or have good thermal stability. These fuels may thus be true "drop in" analogs of their petroleum counterparts and do not require blending to meet current petroleum specifications.

Coupling of the hydrothermolysis reaction and hydrotreating is unique and may result in many process and economic benefits. For example, benefits may include: elimination of a hydrothermolysis product cool down and separation of gas, oil, and water components; elimination of acid water production and treatment; elimination of additional liquid pumping, gas compression, and heat exchange operations for the hydrotreater feed; reduced heat loss; and/or reduced power consumption.

As described above, renewable feedstocks having triacylglycerides-containing oils useful in embodiments disclosed herein may include triacylglycerides-containing oils such as camelina, *carinata, lesquerella*, physaria, jatropha, karanja, moringa, palm, castor, cotton, corn, linseed, peanut, soybean, sunflower, tung, babassu, and canola, or at least one triacylglycerides-containing oil from at least one of, shea butter, tall oil, tallow, waste vegetable oil, algal oil, and pongamia.

Embodiments disclosed herein also relate to the selective use of renewable feedstocks having triacylglycerides containing oils with high concentrations of C20-C24, such as *lesquerella*, physaria, camelina and *carinata*, for the preferential production of jet and diesel fuels.

As the demand for aviation fuels increase worldwide, there is increasing interest in sources other than crude oils derived from petroleum, tar sands, oil shale, and coal for producing said aviation fuels. One such source is what has been termed renewable feedstocks. These renewable feedstocks include but are not limited to: a) plant oils such as canola, coconut, corn, cottonseed, flaxseed, grapeseed, olive, palm, peanut, safflower, sesame, shea, soybean, sunflower, walnut, jatropha; b) animal fasts/oils such as tallow, lard, butterfat; and c) organic wastes such as greases, used cooking oil and sewage sludge. The common feature of these feedstocks for conversion to crude oils is that they are composed of mono-, di-, and triacylglycerides containing their fatty acid backbones in the C10 to C18 carbon number range. Another class of compounds appropriate for these conversion processes are fatty acid alkyl esters especially fatty acid methyl ester (FAME) and fatty acid ethyl ester (FAEE). The aliphatic carbon chains in the glycerides, fatty acids and FAEE can be saturated or mono-, di-, or polyunsaturated, with the latter group being more reactive that that of the saturated group.

The carbon number distributions of some of the above-noted renewable feedstocks are shown in the following table.

TABLE 1

Weight Percent Distribution of Fatty Acids in Various Triacylglycerides Sources

| Renewable Source | Saturated Fatty Acids | | | | | | | | Unsaturated Fatty Acids | | | |
|---|---|---|---|---|---|---|---|---|---|---|---|---|
| | C10 | C12 | C14 | C16 | C18 | C20 | C22 | C24 | C18 | C20 | C22 | C24 |
| almond oil | 0 | 0 | 0 | 7 | 2 | 0 | 0 | 0 | 86 | 0 | 0 | 0 |
| tallow | 0 | 0 | 3 | 24 | 19 | 0 | 0 | 0 | 47 | 0 | 0 | 0 |
| butterfat (cow) | 3 | 3 | 11 | 27 | 12 | 0 | 0 | 0 | 32 | 0 | 0 | 0 |
| canola oil | 0 | 0 | 0 | 4 | 2 | 0 | 0 | 0 | 94 | 0 | 0 | 0 |
| cocoa butter | 0 | 0 | 0 | 25 | 38 | 0 | 0 | 0 | 35 | 0 | 0 | 0 |
| coconut oil | 6 | 47 | 18 | 9 | 3 | 0 | 0 | 0 | 8 | 0 | 0 | 0 |
| corn oil | 0 | 0 | 0 | 11 | 2 | 0 | 0 | 0 | 87 | 0 | 0 | 0 |
| cottonseed oil | 0 | 0 | 1 | 22 | 3 | 0 | 0 | 0 | 74 | 0 | 0 | 0 |
| flaxseed oil | 0 | 0 | 0 | 3 | 7 | 0 | 0 | 0 | 90 | 0 | 0 | 0 |
| grapeseed oil | 0 | 0 | 0 | 8 | 4 | 0 | 0 | 0 | 88 | 0 | 0 | 0 |
| lard | 0 | 0 | 2 | 26 | 14 | 0 | 0 | 0 | 54 | 0 | 0 | 0 |
| olive oil | 0 | 0 | 0 | 13 | 3 | 0 | 0 | 0 | 82 | 0 | 0 | 0 |
| palm oil | 0 | 0 | 1 | 45 | 4 | 0 | 0 | 0 | 50 | 0 | 0 | 0 |
| peanut oil | 0 | 0 | 0 | 11 | 2 | 0 | 0 | 0 | 80 | 0 | 0 | 0 |
| safflower oil | 0 | 0 | 0 | 7 | 2 | 0 | 0 | 0 | 91 | 0 | 0 | 0 |
| sesame oil | 0 | 0 | 0 | 9 | 4 | 0 | 0 | 0 | 86 | 0 | 0 | 0 |
| shea nut | 0 | 1 | 0 | 4 | 39 | 0 | 0 | 0 | 49 | 0 | 0 | 0 |
| soybean oil | 0 | 0 | 0 | 11 | 4 | 0 | 0 | 0 | 85 | 0 | 0 | 0 |
| sunflower oil | 0 | 0 | 0 | 7 | 5 | 0 | 0 | 0 | 88 | 0 | 0 | 0 |
| walnut oil | 0 | 0 | 0 | 11 | 5 | 0 | 0 | 0 | 84 | 0 | 0 | 0 |

The above-noted feedstocks may be used, as described above, for the production of various fuels. However, it has been found that the feedstocks listed in Table 1 may have little productivity for the production of jet fuel range hydrocarbons when subjected to conversion processes that promote cracking-type reactions. A key observation is that these renewable feedstocks are essentially devoid of fatty acids in the carbon number ranges of C20-C24. When processing renewable triacylglycerides containing feedstocks via thermolysis (pyrolysis), hydrothermal (hydrothermal liquefaction or catalytic hydrothermolysis), catalytic hydropyrolysis, or catalytic cracking processes, the cracking of the C10-C18 entities generates high selectivities towards the naphtha and LPG range hydrocarbons, and limited or no selectivity towards jet fuel range hydrocarbons. This can be seen in the following illustrative example:

Using oleic acid (C18) to typify the acyl backbone of the more common triacylglycerides:

$$C_{18}H_{36}O_2 \rightarrow C_{10}H_{20} + C_8H_{16} + (\text{Some Oxygenates})$$

Theoretical (max) Jet Range Precursor yield is 100 mol % (i.e., 1 mol jet range hydrocarbon per mol fatty acid) or 140/284=49.3 wt %.

But when using erucic acid (C22) to typify the acyl backbone of the heavier triacylglycerides:

$$C_{22}H_{44}O_2 \rightarrow C_{10}H_{20} + C_{12}H_{24} \text{ [or 2 } C_{11}H_{22}\text{]} + (\text{Some Oxygenates})$$

Theoretical (max) Jet Range Precursor yield is 200 mol % (i.e., 1 mol jet range hydrocarbon per mol fatty acid) or (140+168)/340=90.5 wt %.

In essence, C20 and higher fatty acids under cracking-type processing can split into 2 mols of jet range products whereas C18 and lighter fatty acids are limited by their chemical stoichiometry to co-producing lower boiling and less desirable naphtha and LPG range hydrocarbons. This translates to higher potential jet range yields for the C20+ fatty acids. In practice, all triacylglycerides derived from plant and animal oils contain some distribution of fatty acids from C10 to C24. *Carinata* and camelina oils, however, have been found to have an exceptional amount of triacylglycerides in the C20 to C24 range. *Carinata* contains more than 55 wt % C20-C24 fatty acid backbone content and Camelina contains more than 25 wt % C20-C24, as shown in Table 2. The plant oils shown in Table 1, in contrast contain very low contents of the C20 and heavier fatty acids. Other oils that may contain a high amount of C20 to C24 triacylglycerides may include *lesquerella* and phyaria oils, among others.

TABLE 2

| Renewable Source | Saturated Fatty Acids | | | | | | | | Unsaturated Fatty Acids | | | |
|---|---|---|---|---|---|---|---|---|---|---|---|---|
| | C10 | C12 | C14 | C16 | C18 | C20 | C22 | C24 | C18 | C20 | C22 | C24 |
| camelina oil | 0 | 0 | 0 | 4.5 | 2.5 | 1.5 | 1 | 0.7 | 66 | 21 | 1 | 1 |
| carinata oil | 0 | 0 | 0 | 2 | 1 | 1 | 0.5 | 0.7 | 38 | 8.5 | 45 | 2.8 |

Since most triacylglycerides containing plant oils and animal fats have as their major contents C14-C18 fatty acid backbones with the C18 fatty acids being the predominant ones, these must first be hydrodeoxygenated (or decarboxylated) to produce n-alkanes in the C14 to C18 range (C13-C17 range for decarboxylation). Then a separate downstream hydrocracking (and sometimes hydroisomerization) step is required to crack the heavier ends, namely, the C18 paraffins, into the jet range. Conventional selective hydrocracking technology is limited to cracking C18s to produce C9s and lighter with a corresponding and significant loss of product to the LPG and naphtha range.

Embodiments disclosed herein relate to the selective use of renewable feedstocks having triacylglycerides containing oils with high concentrations of C20-C24, such as *lesquerella*, physaria, camelina and *carinata*, for the preferential production of jet and diesel fuels. Embodiments disclosed herein also relate to the selective variation of renewable feedstocks to produce hydrocarbons to meet fluctuating demand in the marketplace. For example, during peak gasoline demand, renewable feedstocks or a mixture of renewable feedstocks containing a higher proportion of C16 to C18 triacylglycerides may be used; during periods of lower gasoline demand, or higher jet fuel demand, renewable feedstocks or a mixture of renewable feedstocks containing a higher proportion of C20 to C24 or C22 to C24 triacylglycerides may be used.

In *Carinata*, the olefinic triacylglycerides content represents more than 95% of the total 55% C20-C24 content which is very desirable. Furthermore, the cracking reactivity of the triacylglycerides increases with increasing carbon number meaning that a lower reaction severity can be used to achieve the same conversion of the C20+ olefinic triacylglycerides as that of the C18 and lighter triacylglycerides. The use of a lower reaction severity also translates to reduction in the secondary thermal conversion reactions of the cracked hydrocarbons leading to the production of lighter hydrocarbons in the LPG and naphtha ranges. Alternatively, for the same reaction severity, the C20+ olefinic triacylglycerides will convert at a higher rate than that of the C18 and lighter triacylglycerides.

The use of C20-C24 triacylglycerides maximizes the selectivity of jet range hydrocarbons and jet range oxygenated precursors, thereby promoting the use of opportunity triacylglycerides feedstocks that contain significantly higher contents of C20-C24 fatty acid backbone components. Thus, for a given jet fuel production capacity, the overall renewables feed plant capacity and associated capital costs are significantly lower than those using triacylglycerides feedstocks containing significantly lower contents of C20-C24 fatty acid backbone components.

*Carinata* can produce a theoretical jet range yield of 71.5 wt %, while Camelina can produce a theoretical jet range yield of 55 wt %. Compare these to the 20 most common renewable resources, such as those shown in Table 1, and one can see that these two in particular provide a much higher jet yield than these other renewable sources.

Furthermore, the unsaturates/saturates ratio for *Carinata* (18.7/1) is much higher than that of the 20 renewables feedstocks shown in Table 1, the latter of which have an average ratio of only 5.0/1. The unsaturated triacylglycerides containing olefinic bonds are the most reactive under thermolysis, supercritical hydrothermolysis, hydrothermal liquefaction, catalytic hydropyrolysis or catalytic conversion conditions. In *Carinata*, the olefinic triacylglycerides content represents more than 95% of the total 55% C20-C24 content which is very desirable.

As described with respect to the embodiments of FIGS. 1 and 2, a mixture of the jet-producing triacylglycerides containing oil with water may be reacted at a temperature in the range from about 250° C. to about 560° C. and a pressure greater than about 75 bar to convert at least a portion of the triacylglycerides to a hydrocarbon or mixture of hydrocarbons comprising one or more of jet fuel range hydrocarbons and oxygenated precursors. In some embodiments, the reaction conditions are such that the temperature and pressure are above the supercritical temperature and pressure of water. The resulting reaction effluent may then be further treated and separated to recover the hydrocarbon products.

To form the triacylglycerides/water mixture, a triacylglycerides containing oil may be mixed with water in any fashion. The triacylglycerides/water mixture may have a water to triacylglycerides mass ratio in the range from about 0.001:1 to about 1:1 in some embodiments; from about 0.01:1 to about 1:1 in other embodiments; and from about 0.1:1 to about 1:1 in yet other embodiments.

The reaction effluent may then be directly catalytically hydrotreated, without intermediate separations of water, to form additional jet fuel range hydrocarbons and/or to convert precursors in the reaction effluent to jet fuel range hydrocarbons. In some embodiments, the above-mentioned triacylglycerides containing oils, following hydrothermolysis, may be co-processed in the hydrotreatment zone with other renewable hydrocarbon feedstocks.

Following hydrotreatment, the hydrotreatment effluent may then be processed to separate water and fractionate the hydrocarbons into one or more hydrocarbon fractions, such as those boiling in the range of jet. The water may then be recycled for admixture with the triacylglycerides containing oil as described above.

The reaction of the triacylglycerides to produce jet fuel range hydrocarbons may be primarily one or more hydrothermolysis reactions catalyzed by water and performed at a reaction temperature in the range from about 250° C. to about 560° C. in some embodiments. Reaction conditions may also include a pressure in the range of 50 bar to 300 bar. Conditions of temperature and/or pressure may be selected to be above the critical temperature and/or pressure of water. In all embodiments, the hydrothermolysis reactions may be performed in the absence of added catalysts, such as an inorganic heterogeneous catalyst.

Embodiments disclosed herein may be used, as described above, for the preferential production of jet fuel range products from triacylglycerides-containing oils. For production of jet fuel range products at relatively high proportion, processes for converting triacylglycerides-containing oils into crude oil precursors and/or distillate hydrocarbon fuels according to embodiments herein may include: subjecting one or more triacylglycerides-containing oils to a conversion process to convert at least a portion of the triacylglycerides to produce a reaction product comprising one or more of isoolefins, isoparaffins, cycloolefins, cycloparaffins, and aromatics boiling in the range of naphtha, diesel, and jet fuels.

The proportion of jet fuel range products produced, as noted above, may be varied to meet market demand. Processes disclosed herein may thus also include a step of varying a composition of the triacylglycerides-containing oils to selectively vary a yield of the jet range products. For example, the varying may include increasing or decreasing a content of camelina-based oils, *carinata*-based oils, *lesquerella*-based oils, physaria-based oils, or mixtures thereof in the triacylglycerides-containing oil. The high theoretical jet yield that may be realized from such oils may allow their use in achieving high jet yields from processes disclosed herein as well as to effectively vary the proportion of jet yield products.

The conversion processes that may be used to result in a desired high yield of jet range products according to embodiments herein may include one or more of thermolysis, hydrothermal liquefaction, supercritical hydrothermolysis, catalytic hydropyrolysis, and catalytic cracking. For example, the thermolysis process may be carried out in a fixed-bed, fluidized-bed, or entrained-bed reactor, with or without inert materials, at a temperature in the range from about 300° C. to 600° C., and at space velocities in the range from about 2 to 1000 $h^{-1}$, in the absence of co-fed water. The hydrothermal liquefaction process may be carried out in a fixed-bed, fluidized-bed, or entrained-bed reactor, with or without inert materials, at a temperature in the range from about 150° C. to 370° C., a pressure in the range from about 50 to about 200 bar, and a residence time in the range from about 3 to about 60 minutes, in the presence of co-fed water. The supercritical hydrothermolysis may be carried out in a fixed-bed, fluidized-bed, or entrained-bed reactor, with or without inert materials, at a residence time in the range from about 3 to about 60 minutes at near-critical or supercritical water conditions (e.g., at pressures greater than about 200 bar and/or at temperatures greater than about 370° C.). The catalytic cracking processes may be carried out in entrained-bed reactors using fluid cracking catalysts at a temperature in the range from about 350° C. to 600° C. The catalytic hydropyrolysis may be carried out in a fixed-bed, fluidized-bed, slurry-phase, or entrained-bed reactor, using catalysts comprising one or more of supported or unsupported base metal oxides, silica-aluminas, zeolites, metal phosphides, and hydrotalcites at a temperature in the range from about 300° C. to about 600° C. and a pressure in the range from about 1 to 100 bar. In some embodiments, the conversion process comprises a combination of hydrothermolysis and catalytic cracking.

Following conversion of the triacylglycerides oils according to one or more of the above processes, the recovered hydrocarbons or a portion thereof, such as the jet fuel range hydrocarbons or the C5 to end point hydrocarbons, may be hydrotreated. Hydrotreatment of the reaction product or portion thereof, such as contacting the hydrocarbons at reaction conditions with a catalyst or catalysts comprising one or more metals, metal oxides, and/or metal sulfides, supported or unsupported, having activity for at least one of saturation of olefinic bonds, hydrodeoxygenation, hydrodenitrogenation, and hydrodesulfurization, may be used to upgrade the jet fuel range hydrocarbons to produce specification jet fuel products including one or more of Jet A, Jet A-1, JP-4, JP-5, JP-6, JP-7, JP-8, SPK, and HEFA jet fuels. In some embodiments, the jet fraction may have properties including one or more of: a total acid number of less than 0.1, expressed as mg KOH per gram, and an olefins content of less than about 5 vol % and an aromatics content of less than about 25 vol %. In such instances, the jet fuel range products produced from triacylglycerides-containing oils according to embodiments herein may be used directly as a jet fuel without blending.

In another aspect, embodiments disclosed herein may be used, as described above, for the preferential production of jet fuel range products, such as via hydrothermolysis. For production of jet fuel range products at relatively high proportion, hydrothermolysis processes for converting triacylglycerides-containing oils into crude oil precursors and/or distillate hydrocarbon fuels according to embodiments herein may include: reacting a mixture comprising water, diatomic hydrogen, and a triacylglycerides-containing oil comprising at least 20 wt % C20 to C24 fatty acids at a temperature in the range from about 250° C. to about 560° C. and a pressure greater than about 75 bar to convert at least a portion of the triacylglycerides and recovering a reaction effluent comprising water and one or more of isoolefins, isoparaffins, cycloolefins, cycloparaffins, and aromatics; hydrotreating the reaction effluent to form a hydrotreated effluent.

In some embodiments, the triacylglycerides-containing oil may have a theoretical jet yield of at least 50 wt %, such as in the range from about 50 wt % to about 75 wt %. In some embodiments, the triacylglycerides-containing oil may consist of, or consist essentially of, a renewable oil selected from camelina oil, *carinata* oil, *lesquerella* oil, physaria oil, and mixtures thereof.

EXAMPLES

Two catalytic hydrothermolysis (CH) reaction runs were performed to investigate the effect of co-feeding externally supplied diatomic hydrogen. The reactions were performed in the same reaction system at roughly equivalent operating pressures and temperatures under the following conditions.

| RUN# | H2/CARINATA OIL FEED RATIO, Std L/Gm Oil | PER PASS TAG CONVERSION, Wt % | PER PASS AROMATICS YIELD, Wt % | CH Reactor Pressure, psig | CH Reactor Temperature, C. |
|---|---|---|---|---|---|
| 1 | 0 | 68.4 | 32.6 | 3250 | 468 |
| 2 | 0.26 | 79.7 | 37.6 | 3250 | 470 |

By co-feeding just 0.26 L diatomic hydrogen per gram *Carinata* oil feed, triacylglycerides (TAG) conversion increased by more than 11 percentage points on TAG feed, equivalent to more than a 16% relative increase in conversion performance. Also, total aromatics yield increased some 5 percentage points on TAG feed, equivalent to more than a 15% relative increase in aromatics production performance. Aromatics, especially in the jet fuel fraction, typically exist in petroleum-derived fuels up to a maximum specification of 25 liquid volume percentage in the jet fraction. Therefore another advantage of co-feeding externally supplied diatomic hydrogen is to enhance the aromatics production rate, especially in the jet fuel fraction. The total aromatics yields shown in the table are expressed as percentages on the whole hydrothermolysis crude oil and these values when corrected for the equivalent jet fuel compositions are still within the 25 liquid volume % maximum specification in the jet fuel fraction. While the reaction temperature between the two runs was slightly different, the temperature alone cannot account for the large changes in conversion and aromatics yield, indicating that hydrogen co-feed may have significant advantages.

As described above, embodiments disclosed herein provide processes for the conversion of renewable feedstocks to infrastructure-compatible jet range fuels. The use of C20-C24 triacylglycerides maximizes the selectivity of jet range hydrocarbons and jet range precursors thereby promoting the use of opportunity triacylglycerides-feedstocks that contain significantly higher contents of C20-C24 fatty acid backbone components. Thus, for a given jet fuel production capacity, the overall renewables feed plant capacity and associated capital costs are significantly lower than those using triacylglycerides-feedstocks containing significantly lower contents of C20-C24 fatty acid backbone components.

The processes disclosed herein may be carried out in an economically feasible method at a commercial scale. Embodiments herein may maximize the thermal efficiency of the triacylglycerides containing oil conversion in an economically attractive manner without being hampered by operability problems associated with catalyst fouling. During the hydrothermolysis process, water, such as about 5% of the feed water, may be consumed in the hydrolysis reaction. In the hydrotreater, much of the glycerin byproduct produced may be further hydrogenated and converted to propane. Decarboxylation reactions form COx and that carbon loss may result in a reduced mass yield of liquid products, and an equivalent lower volumetric yield.

Jet fuel range hydrocarbons and oxygenated precursors may be produced by processes disclosed herein. Fuels produced by embodiments herein may: exhibit high density; exhibit high energy density; exhibit good low-temperature properties (freezing point, cloud point, pour point, and viscosity); exhibit natural lubricity; and/or have good thermal stability. These fuels may thus be true "drop in" analogs of their petroleum counterparts and do not require blending to meet current petroleum specifications.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for converting triacylglycerides-containing oils into distillate hydrocarbon fuels, the process comprising:
   preparing a mixture comprising water, diatomic hydrogen, and a triacylglycerides-containing oil comprising at least 20 wt % C20 to C24 fatty acids;
   hydrothermolyzing the mixture at a temperature in a range from about 250° C. to about 560° C. and a pressure greater than about 75 bar to convert at least a portion of the triacylglycerides, wherein the triacylglycerides-containing oil consists essentially of *carinata*, *lesquerella*, physaria, or a mixture thereof to produce a reaction effluent comprising water and one or more of isoolefins, isoparaffins, cycloolefins, cycloparaffins, and aromatics; and
   hydrotreating the reaction effluent to form a hydrotreated effluent comprising the distillate hydrocarbon fuels.

2. The process of claim 1, wherein the triacylglycerides-containing oil has a theoretical jet yield of at least 50 wt %.

3. The process of claim 1, further comprising mixing the triacylglycerides-containing oil with water and diatomic hydrogen to form the mixture.

4. The process of claim 1, further comprising mixing the triacylglycerides-containing oil with water to form a triacylglyceride-water mixture.

5. The process of claim 4, further comprising mixing the triacylglyceride-water mixture with hydrogen to form the mixture.

6. The process of claim 1, wherein the mixture has a water to triacylglycerides mass ratio in a range from about 0.001:1 to about 1:1.

7. The process of claim 1, wherein the mixture has a diatomic hydrogen to triacylglycerides mass ratio in a range from about 0.005:1 to about 0.5:1.

8. The process of claim 1, further comprising separating at least one of diatomic hydrogen and water from the hydrotreated effluent.

9. The process of claim 8, further comprising recycling at least one of the separated diatomic hydrogen and the separated water to the hydrothermolyzing step.

10. The process of claim 1, further comprising co-processing a non-renewable hydrocarbon feedstock with the reaction effluent in the hydrotreating step.

11. The process of claim 1, further comprising fractionating the hydrotreated effluent to recover one or more hydrocarbon fractions boiling in a range of naphtha, diesel, or jet fuel.

12. The process of claim 1, wherein the hydrothermolyzing is performed in the absence of an added heterogeneous or soluble metallic catalyst.

13. The process of claim 1, wherein the hydrothermolyzing is performed in a hydrothermolysis reactor and the process further comprises injecting liquid water into the hydrothermolysis reactor to maintain a temperature or a temperature profile within the hydrothermolysis reactor.

14. The process of claim 11, wherein the hydrocarbon fraction boiling in a range of jet fuel has a total acid number of less than 0.1, expressed as mg KOH per gram.

15. The process of claim 11, wherein the hydrocarbon fraction boiling in a range of jet fuel has an olefins content of less than about 5 vol % and an aromatics content of less than about 25 vol %.

16. The process of claim 11, wherein the hydrocarbon fraction boiling in a range of jet fuel is used directly as a jet fuel without blending; or
   the hydrocarbon fraction boiling in a range of diesel fuel is used directly as a diesel fuel without blending.

17. A process for converting triacylglycerides-containing oils into distillate hydrocarbon fuels, the process comprising:
   subjecting one or more triacylglycerides-containing oils to a conversion process to convert at least a portion of the triacylglycerides into a reaction product comprising one or more of hydrocarbons comprising isoolefins, isoparaffins, cycloolefins, cycloparaffins, and aromatics boiling in ranges of naphtha, diesel, and jet fuels in the presence of water and diatomic hydrogen; and
   varying a composition of the triacylglycerides-containing oils by increasing or decreasing an amount of *carinata*-based oils, *lesquerella*-based oils, physaria-based oils, or a mixture thereof, to selectively vary a yield of hydrocarbons boiling in a range of jet fuel.

18. The process of claim 17, wherein the conversion process comprises thermolysis.

19. The process of claim 18, wherein the thermolysis process is carried out in a fixed-bed reactor, a fluidized-bed reactor, or an entrained-bed reactor, with or without inert materials, at a temperature in a range from about 300° C. to 600° C., and at a space velocity in a range from about 2 to 1000 $h^{-1}$.

20. The process of claim 17, wherein the conversion process comprises hydrothermal liquefaction.

21. The process of claim 20, wherein the hydrothermal liquefaction process is carried out in a fixed-bed reactor, a fluidized-bed reactor, or an entrained-bed reactor, with or without inert materials, at a temperature in a range from about 150° C. to 370° C., a pressure in a range from about 50 to about 200 bar, and a residence time in a range from about 3 to about 60 minutes.

22. The process of claim 17, wherein the conversion process comprises supercritical hydrothermolysis.

23. The process of claim 22, wherein the supercritical hydrothermolysis is carried out in a fixed-bed reactor, a fluidized-bed reactor, or an entrained-bed reactor, with or without inert materials, at a residence time in a range from about 3 to about 60 minutes at supercritical water conditions.

24. The process of claim 17, wherein the conversion process comprises catalytic cracking.

25. The process of claim 24, wherein the catalytic cracking process is carried out in entrained-bed reactors using fluid cracking catalysts at a temperature in a range from about 350° C. to 600° C.

26. The process of claim 17, wherein the conversion process comprises catalytic hydropyrolysis.

27. The process of claim 26, wherein the catalytic hydropyrolysis is carried out in a fixed-bed reactor, a fluidized-bed reactor, a slurry-phase reactor, or an entrained-bed reactor, using catalysts comprising one or more of supported or unsupported base metal oxides, silica-aluminas, zeolites, metal phosphides, and hydrotalcites at a temperature in a range from about 300° C. to about 600° C. and a pressure in a range from about 1 to 100 bar.

28. The process of claim 17, wherein the conversion process comprises a combination of hydrothermolysis and catalytic cracking.

29. The process of claim 17, further comprising hydrotreating the reaction product or a portion thereof to produce specification jet fuel products including one or more of Jet A, Jet A-1, JP-4, JP-5, JP-6, JP-7, JP-8, SPK, and HEFA jet fuels.

30. The process of claim 29, wherein the hydrotreating comprises contacting the reaction product or a portion thereof at reaction conditions with a catalyst comprising one or more metals, metal oxides, and/or metal sulfides, supported or unsupported, having activity for at least one of saturation of olefinic bonds, hydrodeoxygenation, hydrodenitrogenation, and hydrodesulfurization.

31. The process of claim 17, wherein the composition of the triacylglycerides-containing oils further comprises camelina-based oils.

32. A process for converting triacylglycerides-containing oils into distillate hydrocarbon fuels, the process comprising:
preparing a mixture comprising water, diatomic hydrogen, and one or more triacylglycerides-containing oil comprising at least 20 wt % C20 to C24 fatty acids;
hydrothermolyzing the mixture, in the absence of an added heterogeneous or soluble metallic catalyst, at a temperature in a range from about 250° C. to about 560° C. and a pressure greater than about 75 bar to convert at least a portion of the triacylglycerides, producing a reaction effluent comprising water and one or more of isoolefins, isoparaffins, cycloolefins, cycloparaffins, and aromatics; and
hydrotreating the reaction effluent to form a hydrotreated effluent comprising the distillate hydrocarbon fuels.

33. The process of claim 32, wherein the triacylglycerides-containing oil consists essentially of a renewable oil from camelina, *carinata, lesquerella*, physaria, or a mixture thereof.

* * * * *